US009066800B2

(12) United States Patent
Clague et al.

(10) Patent No.: US 9,066,800 B2
(45) Date of Patent: Jun. 30, 2015

(54) DUAL VALVE PROSTHESIS FOR TRANSCATHETER VALVE IMPLANTATION

(75) Inventors: Cynthia Clague, Minnetonka, MN (US); Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 244 days.

(21) Appl. No.: 13/432,664

(22) Filed: Mar. 28, 2012

(65) Prior Publication Data

US 2013/0261738 A1    Oct. 3, 2013

(51) Int. Cl.
    *A61F 2/24* (2006.01)

(52) U.S. Cl.
    CPC ............. *A61F 2/2418* (2013.01); *A61F 2/2412* (2013.01); *A61F 2/2436* (2013.01); *A61F 2220/0091* (2013.01); *A61F 2250/0039* (2013.01); *A61F 2250/006* (2013.01); *A61F 2230/0054* (2013.01); *A61F 2230/008* (2013.01)

(58) Field of Classification Search
    CPC ... A61F 2/2418; A61F 2/2436; A61F 2/2412; A61F 2220/0091; A61F 2250/006
    USPC .......... 623/2.11, 2.18, 2.12, 2.13, 2.14, 2.15, 623/2.16, 2.17, 1.24, 1.25, 1.26
    See application file for complete search history.

(56) References Cited

U.S. PATENT DOCUMENTS

| | | | |
|---|---|---|---|
| 5,957,949 A | | 9/1999 | Leonhardt et al. |
| 6,540,782 B1 * | | 4/2003 | Snyders .................... 623/2.14 |
| 2001/0021872 A1 * | | 9/2001 | Bailey et al. ................ 623/1.24 |
| 2002/0123802 A1 * | | 9/2002 | Snyders .................... 623/2.18 |
| 2003/0040792 A1 * | | 2/2003 | Gabbay .................... 623/2.11 |
| 2004/0210306 A1 | | 10/2004 | Quijano et al. |
| 2005/0256566 A1 | | 11/2005 | Gabbay |
| 2006/0241745 A1 | | 10/2006 | Solem |
| 2006/0259136 A1 * | | 11/2006 | Nguyen et al. ............... 623/2.18 |
| 2008/0071362 A1 | | 3/2008 | Tuval et al. |
| 2008/0183273 A1 | | 7/2008 | Mesana et al. |
| 2009/0248143 A1 | | 10/2009 | Laham |
| 2009/0264991 A1 | | 10/2009 | Paul, Jr. et al. |
| 2009/0276040 A1 * | | 11/2009 | Rowe et al. ................ 623/2.18 |
| 2009/0287299 A1 * | | 11/2009 | Tabor et al. ................ 623/1.26 |
| 2009/0319038 A1 | | 12/2009 | Gurskis et al. |
| 2010/0217382 A1 * | | 8/2010 | Chau et al. .................. 623/1.26 |
| 2010/0298927 A1 * | | 11/2010 | Greenberg .................. 623/1.26 |
| 2011/0106244 A1 * | | 5/2011 | Ferrari et al. ................ 623/2.1 |
| 2011/0208298 A1 * | | 8/2011 | Tuval et al. ................. 623/2.17 |
| 2013/0261737 A1 * | | 10/2013 | Costello .................... 623/2.11 |
| 2013/0261739 A1 * | | 10/2013 | Kuehn ...................... 623/2.11 |

FOREIGN PATENT DOCUMENTS

| | | |
|---|---|---|
| WO | WO2006/111391 | 10/2006 |
| WO | WO2008091515 | 7/2008 |
| WO | WO2009/092782 | 7/2009 |

(Continued)

*Primary Examiner* — Katrina Stransky

(57) ABSTRACT

A dual valve prosthesis having first and second prosthetic valve components with a linkage that connects the first and second prosthetic valve components together is disclosed. Each of the first and second prosthetic valve components includes a stent structure with a prosthetic valve secured therein. In a disclosed method, the first and second prosthetic valve components include prosthetic mitral and aortic valves, respectively, and the dual heart valve prosthesis is configured to replace both the native mitral and aortic valves of the heart in a single transcatheter heart valve implantation procedure. The linkage between the first and second prosthetic valve components is configured to secure the anterior mitral valve leaflet against a wall of the left ventricle when the dual valve prosthesis is implanted within the heart.

18 Claims, 4 Drawing Sheets

(56) References Cited

FOREIGN PATENT DOCUMENTS

| | | |
|---|---|---|
| WO | WO2009092782 | 7/2009 |
| WO | WO2009/126362 | 10/2009 |
| WO | WO2009129481 | 10/2009 |
| WO | WO2012/018599 | 2/2012 |
| WO | WO2013/059747 | 4/2013 |
| WO | WO2013/148019 | 10/2013 |

* cited by examiner

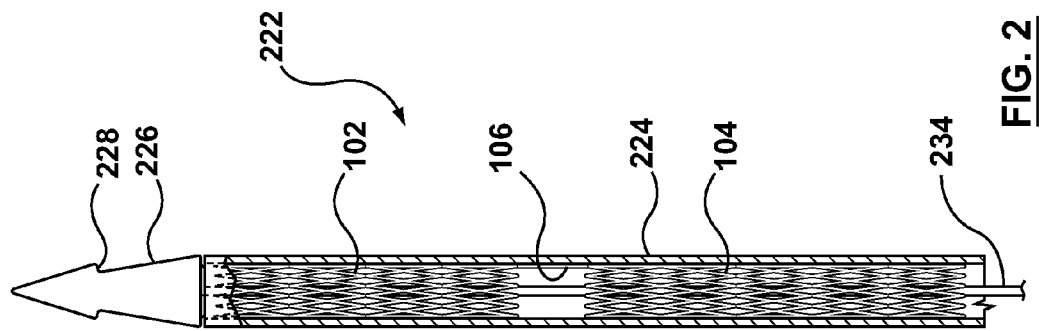
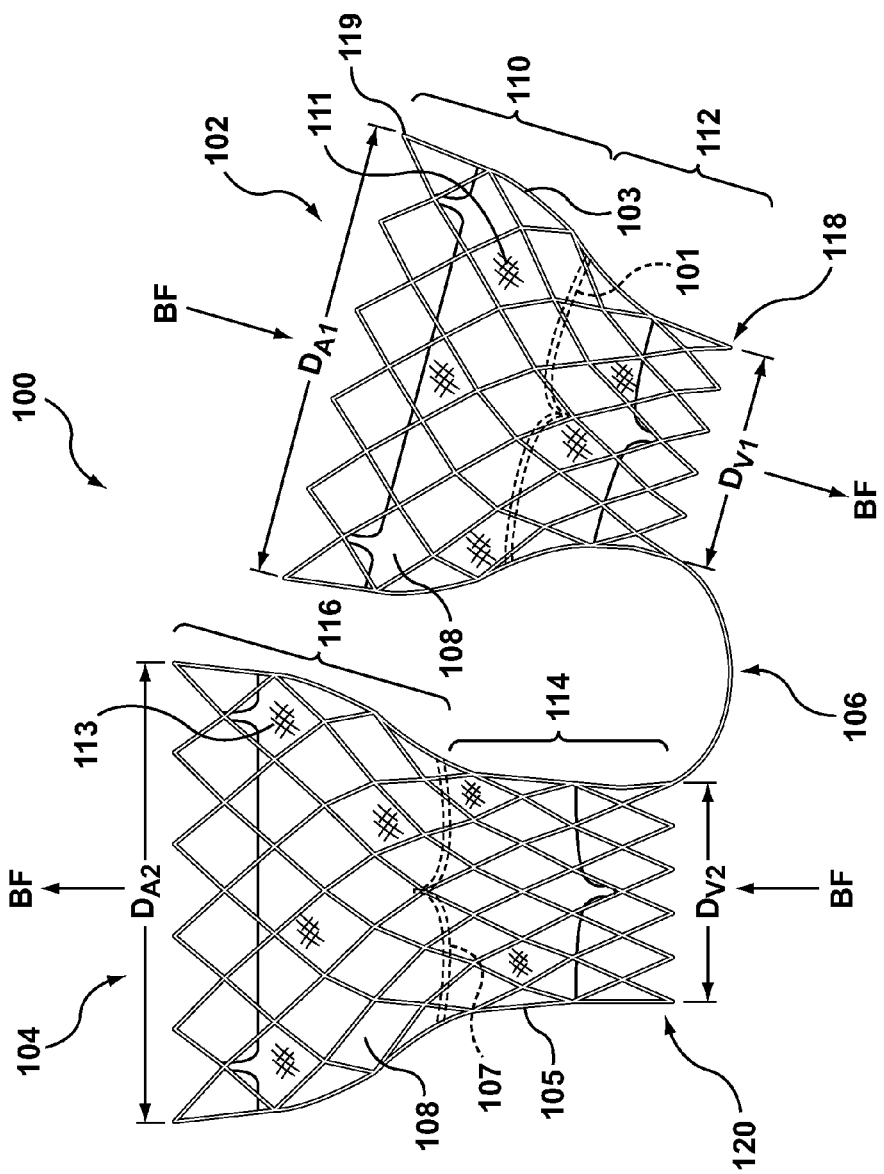

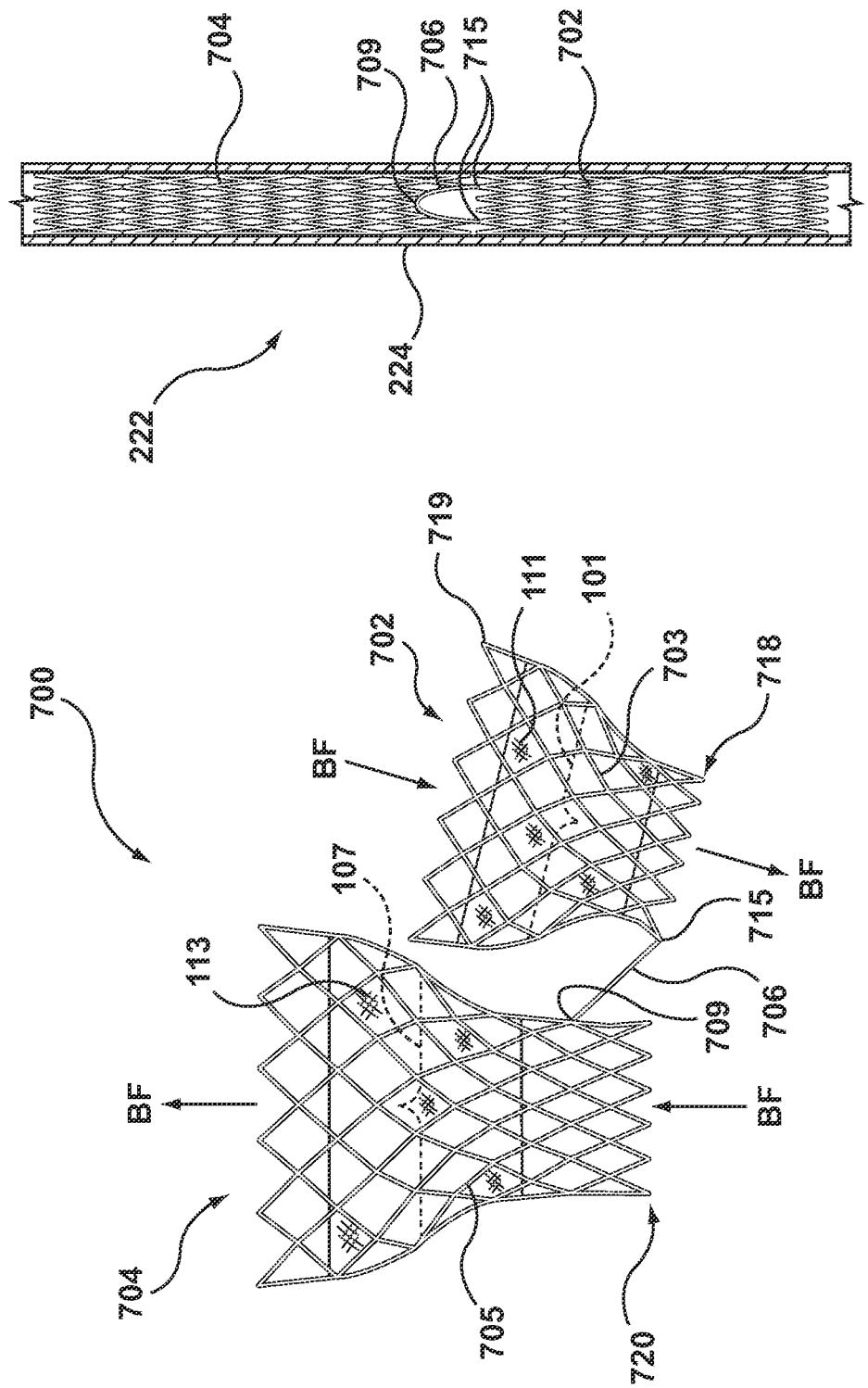

DUAL VALVE PROSTHESIS FOR TRANSCATHETER VALVE IMPLANTATION

FIELD OF THE INVENTION

The invention relates generally to a prosthetic valve for replacing a native valve or a previously implanted prosthetic valve in a non-surgical interventional procedure. More particularly, the invention relates to a dual valve prosthesis having a prosthetic aortic valve combined with a prosthetic mitral valve for concurrently replacing the corresponding native valves or previously implanted prosthetic valves in a non-surgical interventional procedure.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a delivery catheter or by crimping onto a balloon of a dilatation catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent", which is incorporated by reference herein in its entirety.

Valvular heart disease is any disease process involving one or more of the valves of the heart, i.e., the aortic and mitral valves on the left and the pulmonary and tricuspid valves on the right. Severe valve damage may be treated with a valve replacement, with aortic valves and severely damaged mitral valves being the most often replaced heart valves. Some patients present with more than one heart valve being damaged so that the patient may need a dual valve replacement requiring more than one heart valve to be repaired or replaced. Whereas the use of minimally invasive techniques may be preferred, such an approach may be difficult in a dual valve replacement as placement of the prosthetic mitral valve prior to or subsequent of placement of the prosthetic aortic valve may be extremely difficult due to the relative locations of the two native valves, the lack of space in the left ventricle, and/or the concern of having to cross the first deployed prosthetic valve with the second delivery system and prosthetic valve under certain circumstances. Moreover, when a prosthetic valve is percutaneously delivered to replace a stenotic or insufficient aortic or mitral valve, a fundamental concern is that the prosthesis be deployed as precisely as possible so as to assure proper functioning, to avoid paravalvular leakage and to minimize any negative impact on the adjacent heart valve, each of which becomes more difficult to achieve with a dual valve replacement performed using multiple prosthetic valves and delivery devices. Further, sufficient prosthetic mitral valve fixation against high systolic pressures is also particularly important as migration or movement of the mitral valve prosthetic device can potentially block the left ventricular outflow tract or inhibit native or replacement aortic valve function. As such patients who must have a dual valve replacement most often undergo open heart surgical replacement procedures to implant the prosthetic aortic and mitral valves or one of the valves goes untreated. Accordingly a need exists in the art for apparatus and methods that allow a clinician to perform a dual heart valve replacement in a minimally invasive manner.

BRIEF SUMMARY OF THE INVENTION

Embodiments hereof are directed to a dual valve prosthesis having first and second prosthetic valve components with a linkage that connects the first and second prosthetic valve components together. Each of the first and second prosthetic valve components includes a stent structure with a prosthetic valve secured therein. In a method in accordance herewith, the first and second prosthetic valve components include prosthetic mitral and aortic valves, respectively, and the dual heart valve prosthesis is configured to replace both the native mitral and aortic valves of the heart in a single transcatheter heart valve implantation procedure. The linkage between the first and second prosthetic valve components is configured to secure the anterior mitral valve leaflet when the dual valve prosthesis is implanted within the heart as well as to assure a relative position between the first and second prosthetic valve components during deployment and after implantation.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a dual valve prosthesis in an expanded configuration in accordance with an embodiment hereof.

FIG. 2 is a sectional view of a distal portion of a delivery catheter with the dual valve prosthesis of FIG. 1 in a compressed delivery configuration therein.

FIG. 7 is a side view of a dual valve prosthesis in an expanded configuration in accordance with another embodiment hereof.

FIG. 8 is a sectional view of a distal portion of a delivery catheter with the dual valve prosthesis of FIG. 7 in a compressed delivery configuration therein.

DETAILED DESCRIPTION OF THE INVENTION

Figure 3:
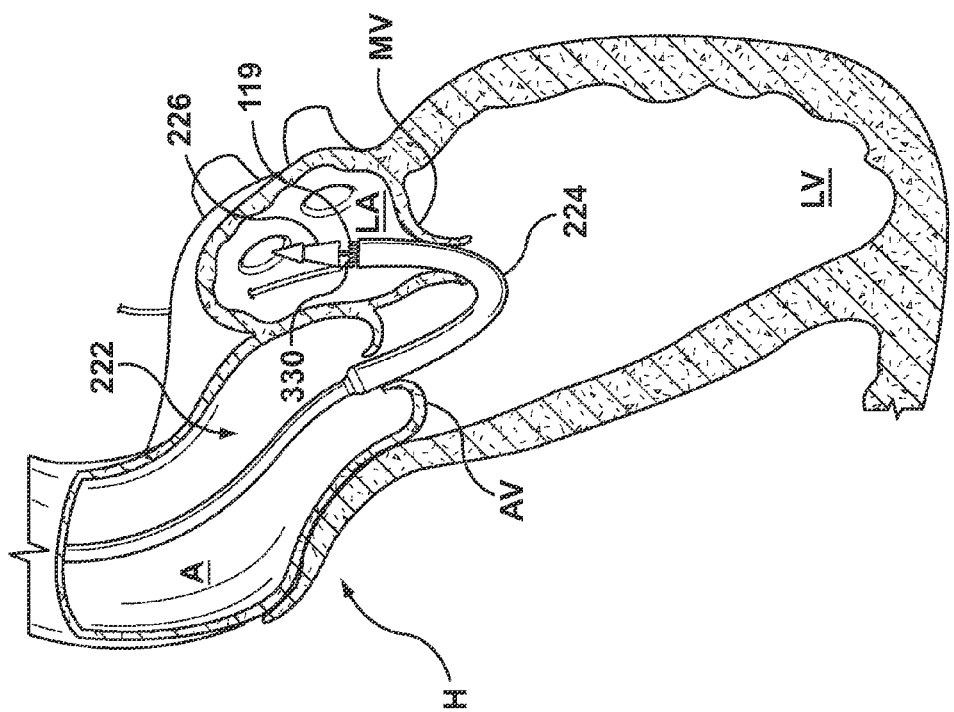
FIGS. 3-6 illustrate a method of performing a concurrent transcatheter valve replacement of the native aortic and mitral valves of a beating heart in accordance with an embodiment hereof.

The following detailed description is merely exemplary in nature and is not intended to limit the invention or the application and uses of the invention. Although the description of embodiments hereof is in the context of concurrent aortic and mitral heart valve replacement, the invention may be adapted to be used for other concurrent valve replacement where it is deemed useful. Furthermore, there is no intention to be bound by any expressed or implied theory presented in the preceding technical field, background, brief summary or the following detailed description.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Further the term "self-expanding" is used in the following description with reference to stent structures of the dual valve prosthesis and is intended to convey that the stent structures are shaped or formed from a material that has a mechanical memory to return to an expanded deployed configuration from a compressed or constricted delivery configuration. Non-exhaustive exemplary materials that may be rendered self-expanding include stainless steel, a pseudo-elastic metal such as a nickel titanium alloy or nitinol, various polymers, and a so-called super alloy, which may have a base metal of nickel, cobalt, chromium, or other metal. Mechanical memory may be imparted to a wire or tubular structure used to form the stent structures by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Embodiments hereof are related to a dual valve prosthesis configured for deployment within the mitral and aortic valves of the heart in a single transcatheter heart valve implantation procedure. FIG. 1 is a side view of a dual valve prosthesis 100 in an expanded configuration in accordance with an embodiment hereof, with FIG. 2 being a sectional view of a distal portion of a delivery catheter 222 with dual valve prosthesis 100 in a compressed delivery configuration therein. Dual valve prosthesis 100 includes a first prosthetic valve component 102 and a second prosthetic valve component 104 having a linkage 106 that extends therebetween. More particularly, linkage 106 laterally extends between a downstream or outflow end 118 of first prosthetic valve component 102 and an upstream or inflow end 120 of second prosthetic valve component 104 to laterally offset one from the other when dual valve prosthesis 100 is in its expanded, deployed configuration. In embodiments hereof, linkage 106 may be one or more strands or strips of a biocompatible material. In an embodiment, linkage 106 may have a rectangular cross-section and be formed to curve upwardly, or in a U-like shape, to bias first prosthetic valve component 102 and second prosthetic valve component 104 toward each other when dual valve prosthesis 100 is in the expanded configuration shown in FIG. 1. In other embodiments, linkage 106 may have a circular cross-section to permit flexing between first prosthetic valve component 102 and second prosthetic valve component 104 when dual valve prosthesis 100 is in the expanded configuration shown in FIG. 1.

The general direction of blood flow through dual valve prosthesis 100 when deployed in vivo is depicted by arrows BF in FIG. 1. Each of first and second prosthetic valve components 102, 104 includes a self-expanding stent structure 103, 105, respectively, with a prosthetic valve 101, 107, respectively, secured therein. Self-expanding stent structures 103, 105 are patterned tubular devices that may be radially compressed into a delivery configuration within a sheath component 224 of delivery catheter 222 for tracking to a treatment site within the heart and thereafter when released from sheath component 224 will return to their expanded configurations shown in FIG. 1.

Figure 6:
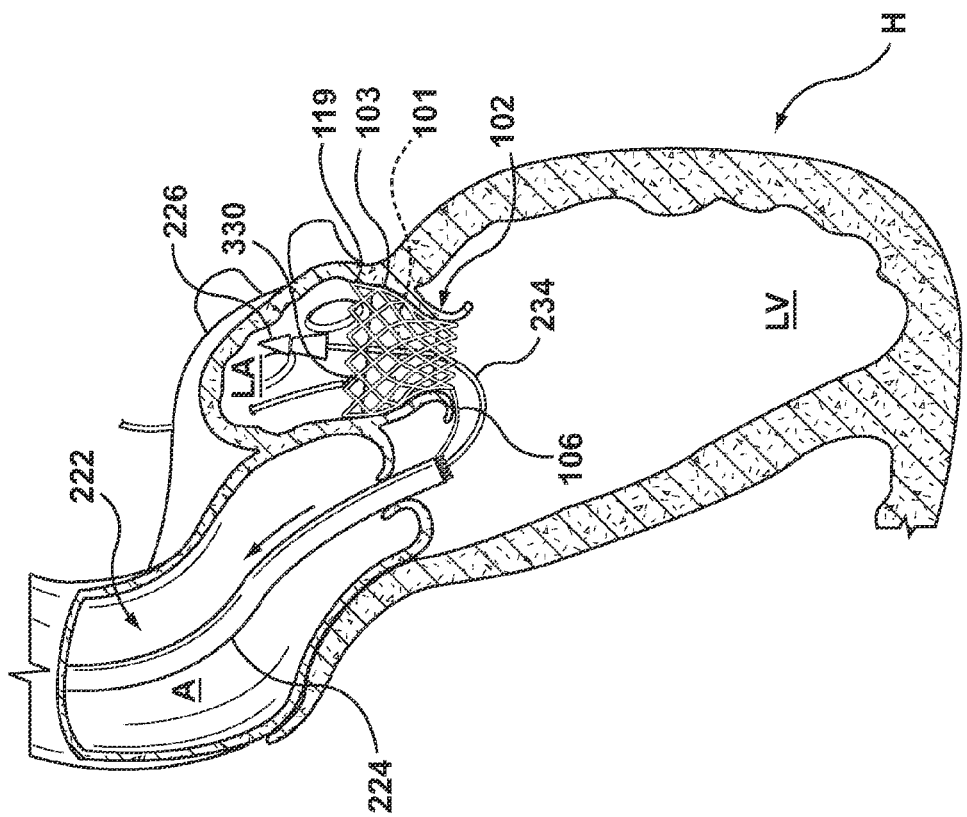

Stent structure 103 has a stepped outer diameter formed by an upstream or atrial segment 110 having an expanded diameter $D_{A1}$ and a downstream or ventricular segment 112 having an expanded diameter $D_{V1}$ which is less than expanded diameter $D_{A1}$. First prosthetic valve component 102 with stent structure 103 is shown deployed at a native mitral valve target site in FIG. 6, with atrial segment 110 expanded into contact with the left atrium and with ventricular segment 112 extending therefrom and expanded into contact with the native mitral valve. In comparison, stent structure 105 has a stepped outer diameter formed by an upstream or ventricular segment 114 having an expanded diameter $D_{V2}$ and a downstream or aortic segment 116 having an expanded diameter $D_{A2}$ which is greater than diameter $D_{V2}$. Second prosthetic valve component 104 with stent structure 105 is shown deployed at a native aortic valve target site in FIG. 6, with aortic segment 116 expanded into contact with the aorta and with ventricular segment 114 extending therefrom and expanded into contact with the native aortic valve. Linkage 106 is also shown in FIG. 6 joining and extending between first and second prosthetic valve components 102, 104 to secure a relative deployed position of one to the other as well as to capture and hold the anterior leaflet of the native mitral valve out of the way of the flow.

In an embodiment, stent structures 103, 105 and linkage 106 may be integrally formed as a unitary structure. In such embodiments, stent structures 103, 105 with integral linkage 106 may be formed by laser cutting or etching the pattern from a tube, such as a tube of nitinol, or from a flat sheet, such as a flat sheet of nitinol, prior to forming the tubular structures. In another embodiment, stent structures 103, 105 may be separately formed with linkage 106 being attached by suture, soldering, laser welding, gluing or any other method of attachment to extend therebetween. In such an embodiment, stent structures 103, 105 may be formed from a plurality of radially-expandable cylindrical rings, which may be constructed of wire, each having a generally zig-zag pattern that have been attached to each other as would be understood by one of ordinary skill in the art. In an embodiment, the cylindrical rings may be attached to a skirt with the desired cylindrical profile, as well as attached to each other with sutures. The linkage 106 may be a strut-like segment attached therebetween by one of the attachment means noted above using the zig-zag ring closest to the ventricle on both stent structures 103, 105. It will be appreciated by one of ordinary skill in the art that the pattern of stent structures 103, 105 of FIG. 1 is merely exemplary and that self-expanding stent structures of various forms, patterns and methods of fabrication can be used as would be apparent to one of skill in the art in accordance with various embodiments of the present invention. Although stent structures 103, 105 are shown in embodiments herein to have openings 108 of a diamond shape, openings of any one of a variety of other shapes may be utilized without departing from the scope hereof.

Prosthetic valves 101, 107 secured within the interior of stent structures 103, 105, respectively, are configured as one-way valves to allow blood flow in one direction and thereby regulate blood flow there through. In the embodiment shown in FIG. 1, each of prosthetic valves 101, 107 includes three valve leaflets to form a tricuspid replacement valve, which may be constructed of pericardium material. In another embodiment, one or both of prosthetic valves 101, 107 may be a bicuspid replacement valve or other leaflet structure that closes with pressure on the outflow and opens with pressure on the inflow. In still other embodiments in accordance herewith, one or both of first and second prosthetic valves 101, 107 may be a single leaflet replacement valve or a replacement valve with more than three leaflets. Natural tissue for forming prosthetic valve leaflets for use in prosthetic valve components in accordance with embodiments hereof may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, Del., polyurethane, Gore-Tex or other cloth materials, nylon blends, polymeric materials, and vacuum deposition nitinol fabricated materials. One polymeric material from which the replacement valve leaflets can be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

The valve leaflets of prosthetic valves 101, 107 are sutured or otherwise securely and sealingly attached to the interior surface of stent structures 103, 105, respectively, and/or graft material 111, 113, respectively, that enclose or line stent structures 103, 105 as would be known to one of ordinary skill in the art of prosthetic valve construction. The graft material 111, 113 may be a low-porosity woven fabric, such as polyester, Dacron fabric, or PTFE, which creates a one-way fluid passage when attached to respective stent structures 103, 105. In one embodiment, graft material 111, 113 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, graft material 111, 113 may instead be of a natural material such as pericardium or another membranous tissue such as intestinal submucosa.

As previously noted above with reference to FIG. 1, the general direction of blood flow through dual valve prosthesis 100 when deployed in vivo is depicted by arrows BF. In an embodiment in which dual valve prosthesis 100 is deployed within the heart, as described in more detail below, first prosthetic valve component 102 is a replacement mitral valve positioned to replace the native mitral valve and second prosthetic valve component 104 is a replacement aortic valve positioned to replace the native aortic valve with linkage 106 extending therebetween to maintain the relative deployed positions of first and second prosthetic valve components 102, 104. Linkage 106 so positioned secures the anterior leaflet of the native mitral valve to prevent the leaflet from interfering with the operation of the replacement prosthetic mitral and/or aortic valves.

FIGS. 3-6 illustrate a method of performing a concurrent transcatheter valve replacement of the aortic valve and mitral valve of a beating heart in accordance with an embodiment hereof. With reference to FIG. 2, delivery catheter 222 includes a distal tip 226 having a necked portion 228 that is attached to an inner shaft component 234, which extends within sheath component 224 to a proximal end of delivery catheter 222 to be assessable by a clinician. In an embodiment hereof, distal tip 226 is a molded polymeric piece having a shoulder formed therein to define necked portion 228 and is configured to be releasably coupled to a distal end of sheath component 224. Dual valve prosthesis 100 is compressed in a delivery configuration within sheath component 224 with first and second prosthetic valve components 102, 104 being sequentially loaded into sheath component 224 and linkage 106 extending therebetween. More particularly, self-expanding stent structures 103, 105 thereof are held in a compressed state by sheath component 224.

Distal tip 226 and sheath component 224 of delivery catheter 222 are shown in FIG. 3 after having been introduced into the vasculature via a percutaneous entry point, which may have been made using the Seldinger technique, and after having been tracked into the left ventricle LV via the aorta. In an embodiment hereof, delivery catheter 222 has been delivered or tracked retrograde through the aorta A and the native aortic valve AV into the left ventricle, after initial access to the vasculature has been made through a percutaneous entry point formed in one of a femoral and subclavian artery or directly through the aorta, which is known as a direct aortic approach, such that delivery catheter 222 has followed one of a transfemoral and subclavian or direct approach to the aorta. In an embodiment hereof, delivery catheter 222 may have been tracked through the vasculature to the left ventricle over a previously placed guidewire (not shown).

Figure 4:
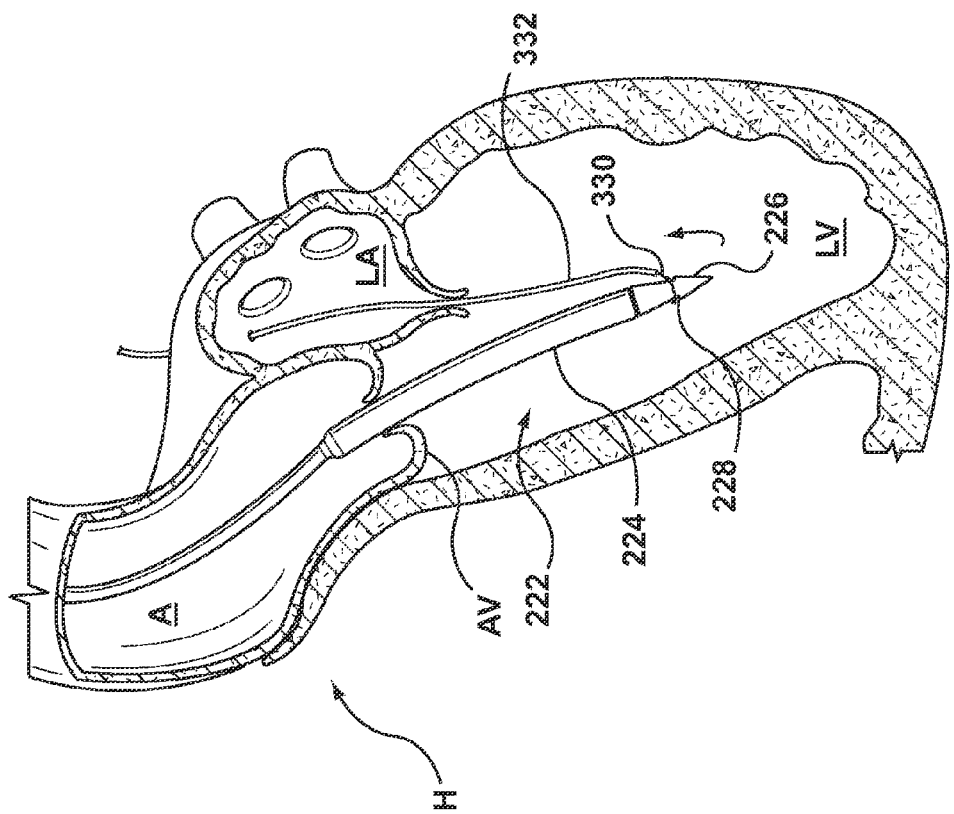
Figure 5:
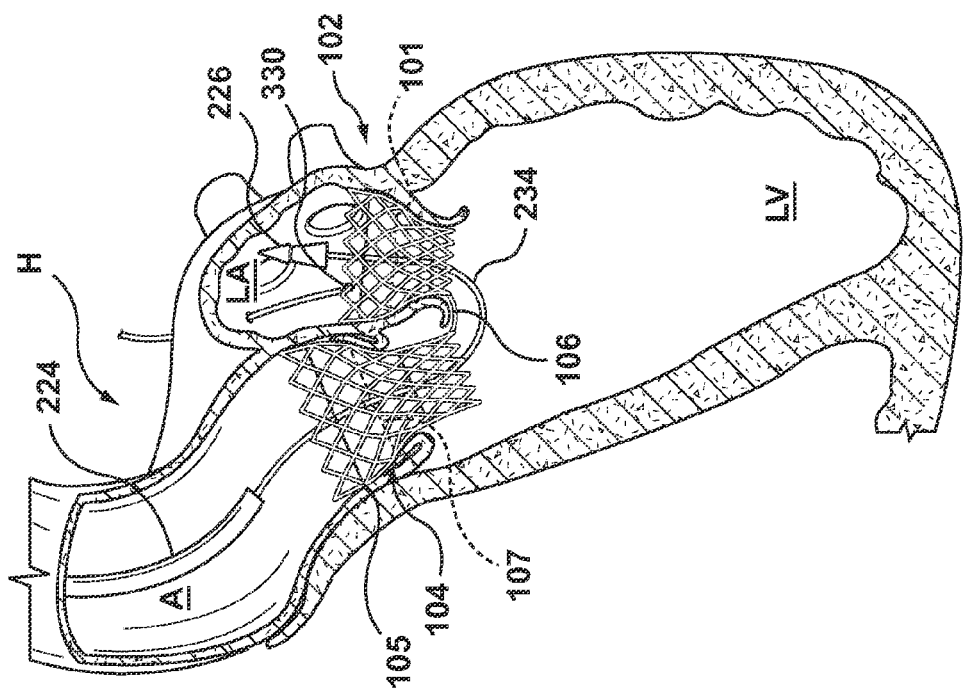

A snare component 330 is positioned to extend through the left atrium LA and native mitral valve MV in FIG. 3. Snare component 330 is a loop of wire or filament that is configured to be tightened around necked portion 228 of delivery catheter distal tip 226 and to secure an upstream or inflow end 119 of first prosthetic valve component 102 during deployment of the first and second prosthetic valve components 102, 104 as explained in detail below. Snare component 330 has a length that extends through a tubular shaft 332 with a proximal end (not shown) that is accessible by a clinician, which allows the loop of snare component 330 to open and close and lock into a closed position. In embodiments hereof, snare component 330 may be delivered through a separate steerable catheter or tubular shaft 332 of snare component 330 may be configured as the steerable component. In either case the steering may be activated at a proximal end of the device by the clinician to allow a distal end of snare component 330 to be guided around the interior of the heart. In an embodiment hereof, a transseptal puncture is made to permit snare component 330 to be advanced or tracked through the left atrium and the native mitral valve into the left ventricle. In another embodiment, snare component 330 may be delivered through the transfemoral vein and through the atrial septum to be advanced or tracked through the left atrium and the native mitral valve into the left ventricle. Snare component 330 is used to snare or otherwise securely catch distal tip 226 of delivery catheter 222 around necked portion 228 such that proximal retraction of the snare component pulls the delivery catheter toward the left atrium and through the native mitral valve. In this manner, snare component 330 is used to position first prosthetic valve component 102 disposed within sheath component 224 of delivery catheter 222 to extend through the native mitral valve, as shown in FIG. 4. Snare component 330 may be left attached to distal tip 226 to provide additional support to delivery catheter 222 as sheath component 224 is retracted. Alternatively, snare component 330 may be detached from delivery catheter distal tip 226 by loosening the loop. In an embodiment in accordance herewith, thereafter snare component 330 may be distally advanced to snare or otherwise securely catch upstream end 119 of first prosthetic valve component 102. With respect to such an embodiment, one or more crowns on inflow end 119 of first prosthetic valve component 102 may have a bulb or otherwise larger area formed thereon which may be ensnared by the loop of snare component 330. In this manner, snare component 330 is used to hold first prosthetic heart valve component 102 in a substantially fixed longitudinal position relative to the native mitral valve while sheath component 224 of delivery catheter 222 is proximally retracted by the clinician, as shown in FIG. 5. Instead of using a snare component to assist with positioning, the dual valve prosthesis could be delivered on a delivery catheter with a steerable tip and a sheath component. The tip could be directed to a position within the first native valve and the first prosthetic valve unsheathed and then could be directed to or held in a position within the second native valve and the second prosthetic valve unsheathed.

Upon initial proximal retraction of sheath component 224, self-expanding stent structure 103 is uncovered and released to return to its expanded configuration such that atrial segment 110 expands into apposition with a wall of the left atrium that surrounds the native mitral valve and such that ventricular segment 112 expands into contact with an annulus of the native mitral valve to extend through the native mitral valve into the left ventricle. Deployed in this manner, prosthetic mitral valve 101 of first prosthetic heart valve component 102 is implanted substantially within the mitral valve annulus. Continued proximal retraction of delivery catheter sheath component 224 releases linkage 106, which is oriented within sheath component 224 such that when released therefrom linkage 106 captures the anterior leaflet of the native mitral valve and prevents the anterior leaflet from interfering with the operation of first and second prosthetic heart valve components 102, 104. In an embodiment, positioning and deployment of first prosthetic heart valve component 102 within the native mitral valve is controlled by the clinician to occur when the heart is in diastole such that linkage 106 captures and pushes the anterior leaflet of the native mitral valve toward and/or against the ventricle wall.

With continued proximal retraction as shown in FIG. 6, self-expanding stent structure 105 of second prosthetic heart valve component 104 is uncovered and released from sheath component 224 to return to its expanded configuration. More particularly, aortic segment 116 of stent structure 105 expands into apposition with a wall of the aorta in the sinus region of the native aortic valve while ventricular segment 114 of stent structure 105 expands into contact with an annulus of the native aortic valve to extend through the native aortic valve into the left ventricle. Deployed in this manner, prosthetic aortic valve 107 of second prosthetic heart valve component 104 is implanted substantially within the aortic valve annulus with the prosthetic leaflets being at or above the level of the native aortic annulus. After implantation of dual valve prosthesis 100, delivery catheter 222 and snare component 330 are removed from the heart.

In an embodiment hereof, snare component 330 may be used to hold first prosthetic heart valve component 102 in a substantially fixed longitudinal position relative to the native mitral valve while sheath component 224 of delivery catheter 222 is proximally retracted by the clinician from covering second prosthetic heart valve component 104, as shown in FIGS. 5 and 6. In another embodiment hereof, the anchoring of stent structure 103 of first prosthetic heart valve component 102 within the structure of the heart as noted above is sufficient to prevent displacement thereof during the subsequent proximal retraction of sheath component 224 and deployment of second prosthetic heart valve component 104 within the native aortic valve. In another embodiment, distal tip 226 of delivery catheter 222 may be modified to include a stent end capture configuration as described in U.S. Pat. Appl. Pub. No. 2009/0276027 to Glynn, which is hereby incorporated by reference herein in its entirety, that may be used to retain one or two crowns on upstream end 119 of first prosthetic valve component 102 during deployment thereof, as the remainder of upstream end 119 will be permitted to deploy to at or near full deployment diameter in order to seat first prosthetic valve component 102 within the mitral valve annulus, and the one or two crowns may continue to be held during the subsequent deployment of second prosthetic valve component 104.

FIG. 6 depicts dual valve prosthesis 100 implanted within the heart H with first prosthetic valve component 102 implanted to replace the native mitral valve and second prosthetic valve component 104 implanted to replace the native aortic valve. With a comparison of FIG. 1 and FIG. 6, prosthetic mitral valve 101 is a one-way valve that is configured to be positioned in the heart between the left atrium and left ventricle to permit blood flow through inflow end 119 of first prosthetic valve component 102 in the direction of arrows BF during atrial emptying and ventricular filling when the leaflets of prosthetic mitral valve 101 are configured to open or part toward the left ventricle. Prosthetic aortic valve 107 is a one-way valve that is configured to be positioned in the heart between the left ventricle and the aorta to permit blood flow through inflow end 120 of second prosthetic valve component 104 in the direction of arrows BF during systole when the leaflets of prosthetic aortic valve 107 are configured to open or part toward the aorta. Linkage 106 anchors first and second prosthetic valve components 102, 104 to each other allowing one to support and stabilize the other during the heart beat in vivo. More particularly, the pressures on prosthetic mitral valve 101 and prosthetic aortic valve 107 will be asynchronous during the normal beating of the heart so when one prosthetic valve is closed and being pushed by fluid pressure the other prosthetic valve is open. The pressure on the closed prosthetic valve pushing on the prosthesis is countered by linkage 106 helping to prevent migration of the prosthesis. If first and second prosthetic valve components 102, 104 were separate without a linkage, the stent frames thereof might overlap and interfere with one another causing possible instability and wear. In embodiments hereof, each of prosthetic mitral valve 101 and prosthetic aortic valve 107 may be a bioprosthetic trileaflet heart valve such as any one of the bioprosthetic heart valves being used in implantable heart valve devices currently available that has been adapted for use herein.

FIG. 7 depicts a side view of a dual valve prosthesis 700 in an expanded configuration in accordance with another embodiment hereof, with FIG. 8 being a sectional view of the distal portion of delivery catheter 222 with dual valve prosthesis 700 in a compressed delivery configuration therein. Features and aspects of the prior embodiment described herein may be used accordingly with the current embodiment and the same reference numbers are used for features of dual valve prosthesis 700 that remain unchanged from dual valve prosthesis 100 described above, as such those features are not further described in detail herein. Dual valve prosthesis 700 includes first prosthetic valve component 702 and second prosthetic valve component 704 having a linkage or support arm 706 that laterally extends therebetween when the dual valve prosthesis is in an expanded configuration. In contrast to the previous embodiment, linkage 706 forms a portion of an upstream or inflow end 720 of stent structure 705 of second prosthetic valve component 704 that is attached to or integrally formed with a downstream or outflow end 718 of a stent structure 703 of first prosthetic valve component 702 at one or more joints 715. Linkage 706, which may have the patterned structure of stent structure 705, is configured to pivot outwardly from the remainder of stent structure 705 at a hinge 709 and to bend at joint(s) 715 to permit first and second prosthetic valve components 702, 704 to be laterally offset one from the other when dual valve prosthesis 700 is in an expanded, deployed configuration. In an embodiment, joint(s) 715 may be created such that instead of being linkage 706 being formed as one piece with stent structure 705, the two prosthetic valve components 702, 704 are attached at the two ends of linkage 706 by loops on the linkage ends that are formed to encase at least two of the crowns on the opposite stent. In an embodiment, hinged linkage 706 is configured to permit radial and axial flexing between first prosthetic valve component 702 and second prosthetic valve component 704 when dual valve prosthesis 100 is deployed in vivo. The nature of linkage 706 being partially detached from stent structure 705 allows linkage 706 to move separately therefrom, which permits each of first and second prosthetic valve components 702, 704 to flex up and down and back and forth relative to one another. Additionally, the U-shape of linkage 706 creates a clearance area with second prosthetic valve component 704 that allows the outflow area of first prosthetic valve component 702 to move back and forth inside the clearance area when both valve components are fully deployed. The advantage being that this configuration allows prosthetic valve components 702, 704 to move independent of each other without interfering with each other and therefore avoids any distortion of the annular region shape which could interfere with leaflet function.

The general direction of blood flow through dual valve prosthesis 700 when deployed in vivo is depicted by arrows BF in FIG. 7. Each of first and second prosthetic valve components 702, 704 includes stent structure 703, 705, respectively, with prosthetic valve 101, 107, respectively, secured therein. Stent structures 703, 705 are self-expanding patterned tubular devices that may be radially compressed into a delivery configuration within delivery catheter sheath component 224 for tracking to a treatment site within the heart and thereafter when released from sheath component 224 will return to their expanded configurations shown in FIG. 7.

Stent structures 703, 705 each have stepped outer diameters with either an upstream or downstream segment thereof having an expanded diameter that is greater than an expanded diameter of a corresponding downstream or upstream segment of the stent structures, as explained in detail above with respect to stent structures 103, 105. When first prosthetic valve component 702 with stent structure 703 is deployed at a native mitral valve target site, the large diameter upstream segment expands into contact with the left atrium such that the narrower downstream segment extends therefrom to expand into contact with the native mitral valve. In comparison, when second prosthetic valve component 704 with stent structure 705 is deployed at a native aortic valve target site, the large diameter downstream segment expands into contact with the aorta such that the narrower upstream segment extends therefrom to expand into contact with the native aortic valve. When dual valve prosthesis 700 is deployed in such a manner, linkage 706 outwardly hinges from stent structure 705 to extend between first and second prosthetic valve components 702, 704 and thereby secures a relative deployed position of one to the other as well as captures and holds the anterior leaflet of the native mitral valve preventing interference with flow through the bioprosthetic valves.

In an embodiment, linkage 706 and stent structures 703, 705 may be integrally formed as a unitary structure. In such an embodiment, stent structures 703, 705 with integral linkage 706 may be formed by etching the pattern from a tube, such as a tube of nitinol, or from a flat sheet, such as a flat sheet of nitinol, prior to forming the tubular structures. In another embodiment, stent structures 703, 705 may be separately formed with linkage 706 being an integral part of stent structure 705 and being separately attached to stent structure 703. It will be appreciated by one of ordinary skill in the art that the pattern of stent structures 703, 705 of FIG. 1 is merely exemplary and that self-expanding stent structures of various forms, patterns and methods of fabrication can be used as would be understood by one of ordinary skill in the art in accordance with various embodiments of the present invention.

Dual valve prosthesis 700 may be compressed in a delivery configuration within sheath component 224 with first and second prosthetic valve components 702, 704 being sequentially loaded into sheath component 224 with linkage 706 therebetween such that self-expanding stent structures 703, 705 thereof are held in a compressed state by the sheath component. Dual valve prosthesis 700 may be implanted within the heart H in a single transcatheter procedure as described above for dual valve prosthesis 100 with first prosthetic valve component 702 being implanted to replace the native mitral valve and second prosthetic valve component 704 implanted to replace the native aortic valve. With reference to FIG. 7, prosthetic mitral valve 101 is a one-way valve that is configured to be positioned in the heart between the left atrium and left ventricle to permit blood flow through inflow end 719 of first prosthetic valve component 702 in the direction of arrows BF during atrial emptying and ventricular filling when the leaflets of prosthetic mitral valve 101 are configured to open or part toward the left ventricle. Prosthetic aortic valve 107 is a one-way valve that is configured to be positioned in the heart between the left ventricle and the aorta to permit blood flow through inflow end 720 of second prosthetic valve component 704 in the direction of arrows BF during systole when the leaflets of prosthetic aortic valve 107 are configured to open or part toward the aorta.

Dual valve prosthesis in accordance with embodiments hereof may be deployed within native mitral and aortic valves and/or previously implanted prosthetic valves therein via one of the Medtronic CoreValve® delivery system with Accu-Trak™ Stability Layer or the Engager™ Transcatheter Aortic Valve Implantation System, each of which is a heart valve delivery system developed by Medtronic, Inc. of Minneapolis, Minn. that may be adapted for use in embodiments hereof.

Although each of stent structures 103, 703 of first prosthetic valve components 102, 702 are shown in embodiments hereof to be shorter than correspondingly linked stent structures 105, 705 of second prosthetic valve components 104, 704, respectively, this is by way of illustration and not limitation. In other embodiments in accordance herewith, stent structures 103, 703 of first prosthetic valve components 102, 702 may of equal or greater length than correspondingly linked stent structures 105, 705 of second prosthetic valve components 104, 704, respectively.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A dual heart valve prosthesis comprising:
   a first prosthetic heart valve component for implanting within a first native heart valve having a first stent structure with a first prosthetic heart valve secured therein, wherein when the first prosthetic heart valve component is in an expanded configuration the first stent structure has an upstream segment with a greater expanded diameter than a downstream segment thereof;
   a second prosthetic heart valve component for implanting within a second native heart valve having a second stent structure with a second prosthetic heart valve secured therein, wherein when the second prosthetic heart valve component is in an expanded configuration the second stent structure has a downstream segment with a greater expanded diameter than an upstream segment; and
   a linkage laterally extending between the first and second stent structures that connects the first and second prosthetic heart valve components together, wherein the linkage laterally extends between a downstream end of the first prosthetic heart valve component and an upstream end of the second prosthetic heart valve, and wherein the linkage is configured for contacting a portion of the heart disposed between the first and second native heart valves when the dual heart valve prosthesis is implanted within the heart.

2. The dual heart valve prosthesis of claim 1, wherein the linkage is comprised of one or more strands.

3. The dual heart valve prosthesis of claim 1, wherein the linkage is a hinged segment of the second stent structure that is configured to pivot outwardly from the upstream end of the second stent structure.

4. The dual heart valve prosthesis of claim 1, wherein the first and second stent structures are self-expanding.

5. The dual heart valve prosthesis of claim 1, wherein when the dual heart valve prosthesis is in a deployed configuration the linkage biases the first and second prosthetic heart valve components toward each other.

6. A method of implanting a dual heart valve prosthesis within a beating heart comprising:
   introducing a delivery catheter into the left ventricle of the heart, wherein a dual heart valve prosthesis having first and second prosthetic heart valve components connected by a linkage is disposed within a distal portion of the delivery catheter, wherein the linkage laterally extends between a downstream end of the first prosthetic heart valve component and an upstream end of the second prosthetic heart valve component;
   deploying the first prosthetic heart valve component within the native mitral valve; and
   deploying the second prosthetic heart valve component within the native aortic valve, such that the linkage connecting the first and second prosthetic heart valve components pushes the anterior leaflet of the native mitral valve against the wall of the left ventricle.

7. The method of claim 6, wherein the first prosthetic heart valve component includes a first stent structure with a prosthetic mitral valve secured therein and the second prosthetic heart valve component includes a second stent structure with a prosthetic aortic valve secured therein.

8. The method of claim 7, wherein the first and second stent structures are self-expanding and wherein the delivery catheter includes a sheath component such that during the step of introducing the delivery catheter the first and second stent structures are compressed in a delivery configuration within the distal portion of the delivery catheter by the sheath component.

9. The method of claim 8, wherein each of the steps of deploying the first and second prosthetic heart valve components within the native mitral valve and native aortic valve, respectively, includes proximally retracting the sheath component of the delivery catheter.

10. The method of claim 6, wherein the step of deploying the first prosthetic heart valve component occurs when the heart is in diastole.

11. The method of claim 6, wherein the step of introducing the delivery catheter into the left ventricle includes accessing the aorta via a transfemoral, subclavian or direct aortic approach and tracking the distal portion of the delivery catheter through the aorta and the native aortic valve into the left ventricle.

12. The method of claim 6 further comprising:
   snaring a distal tip of the delivery catheter with a snare component when the distal tip of the delivery catheter is within the left ventricle;
   pulling the delivery catheter with the snare component toward the left atrium; and positioning the first prosthetic valve component disposed within the distal portion of the delivery catheter to extend through the native mitral valve.

13. The method of claim 12, wherein the step of snaring includes
   creating a transeptal puncture,
   introducing the snare component into the left atrium via the transeptal puncture, and
   advancing the snare component through the native mitral valve into the left ventricle.

14. The method of claim 12, further comprising:
   detaching the snare component from the delivery catheter distal tip; and using the snare component to hold the first prosthetic heart valve component in place within the native mitral valve while the delivery catheter is proximally retracted.

15. The method of claim 14, wherein the steps of deploying the first and second prosthetic heart valve components within the native mitral valve and native aortic valve, respectively occur as at least a sheath component of the delivery catheter is proximally retracted.

16. A dual heart valve prosthesis comprising:
a prosthetic mitral valve component for implanting within the native mitral valve having a stent structure with a prosthetic mitral valve secured therein, wherein the stent structure of the prosthetic mitral valve component in an expanded configuration has an upstream segment with a greater expanded diameter than a downstream segment thereof;
a prosthetic aortic valve component for implanting within the native aortic valve having a stent structure with a prosthetic aortic valve secured therein, wherein the stent structure of the prosthetic aortic valve component in an expanded configuration has a downstream segment with a greater expanded diameter than an upstream segment thereof; and
a linkage that laterally extends between an outflow end of the prosthetic mitral valve component and an inflow end of the prosthetic aortic valve component to connect the respective stent structures together, wherein the linkage is configured for contacting the anterior leaflet of the native mitral valve within the left ventricle when the dual heart valve prosthesis is implanted within the heart.

17. The dual heart valve prosthesis of claim 16, wherein when the prosthetic mitral valve component is implanted within the native mitral valve in the expanded configuration the upstream segment of the stent structure is configured to contact the left atrium and the downstream segment of the stent structure is configured to extend within and contact the native mitral valve.

18. The dual heart valve prosthesis of claim 17, wherein when the prosthetic aortic valve component is implanted within the native aortic valve in the expanded configuration the downstream segment of the stent structure is configured to contact a wall of the aorta and the upstream segment of the stent structure is configured to extend within and contact the native aortic valve.

* * * * *